United States Patent [19]

Hodorek

[11] Patent Number: 5,167,664
[45] Date of Patent: Dec. 1, 1992

[54] RATCHETING BONE SCREW

[75] Inventor: Robert A. Hodorek, Warsaw, Ind.

[73] Assignee: Zimmer, Inc., Warsaw, Ind.

[21] Appl. No.: 801,217

[22] Filed: Dec. 2, 1991

Related U.S. Application Data

[63] Continuation-in-part of Ser. No. 749,766, Aug. 26, 1991, abandoned.

[51] Int. Cl.[5] .............................................. A61F 5/04
[52] U.S. Cl. .......................................... 606/73; 623/16
[58] Field of Search .................... 623/16, 18; 411/339, 411/338, 411, 508–510; 606/65, 69, 73, 72, 61

[56] References Cited

U.S. PATENT DOCUMENTS

| Re. 33,348 | 9/1990 | Lower | 606/65 |
|---|---|---|---|
| 3,990,438 | 11/1976 | Pritchard | 606/65 |
| 4,456,005 | 6/1984 | Lichty | 606/65 |
| 4,611,581 | 9/1986 | Steffee | 606/73 |
| 4,759,670 | 7/1988 | Linder et al. | 411/43 |
| 4,796,612 | 1/1989 | Reese | 606/72 |
| 5,085,660 | 2/1992 | Lin | 606/69 |

Primary Examiner—David Isabella
Attorney, Agent, or Firm—Todd A. Dawson

[57] ABSTRACT

A two piece bone screw having a separate head and shaft adapted for slidable engagement relative to one another. The head and shaft include a plurality of teeth which mutually engage to permit the head to shift relative to the shaft in only one direction. Therefore, under load, the head is shifted downwardly along the shaft to shorten the length of the screw in a ratcheting manner.

1 Claim, 2 Drawing Sheets

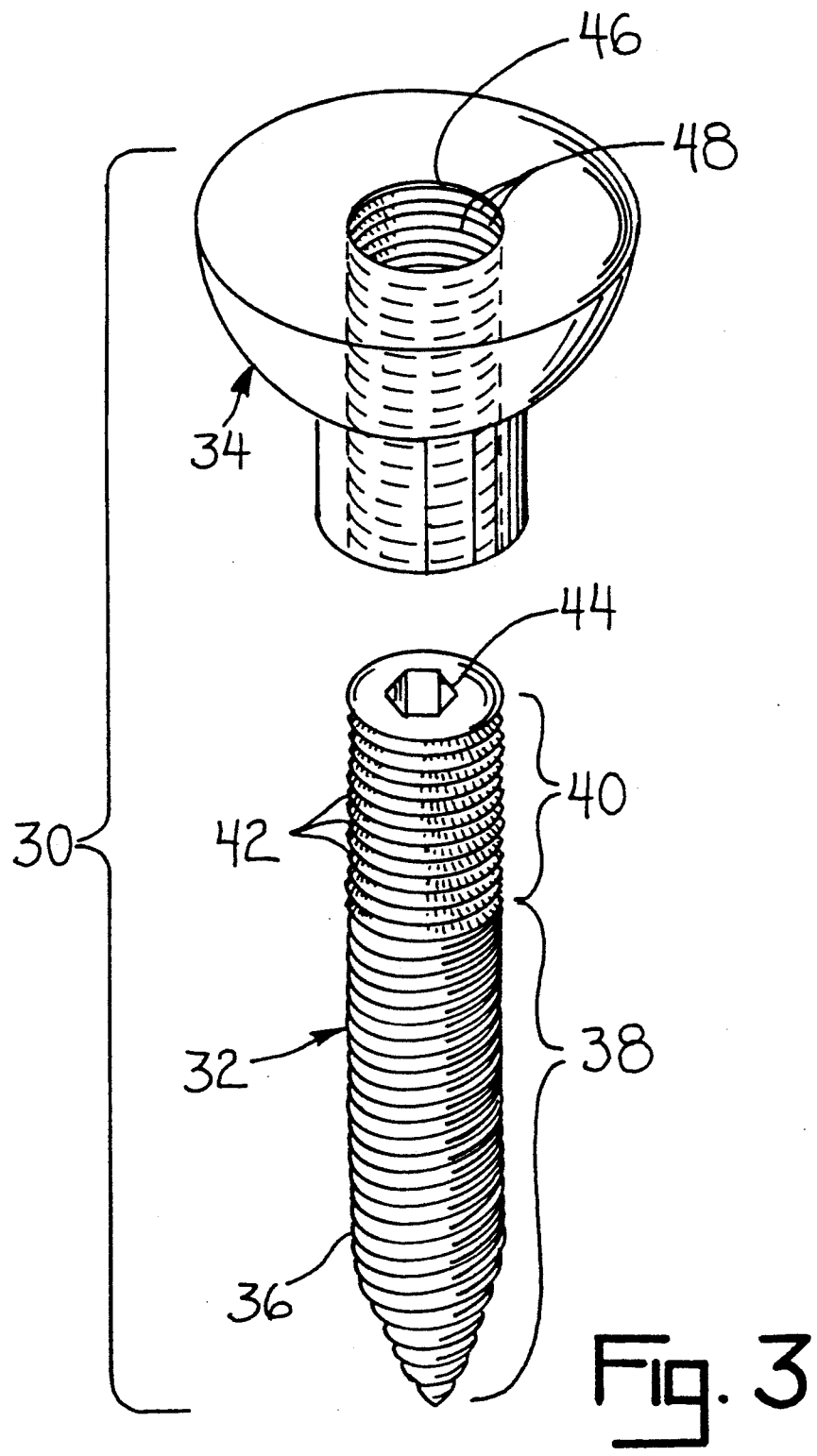

RATCHETING BONE SCREW

RELATED APPLICATION

This Application is a continuation-in-part of U.S. patent Ser. No. 07/749,766 filed on Aug. 26, 1991, now abandoned.

SUMMARY OF THE INVENTION

This invention relates to a bone screw and more specifically to a bone screw having a head and shaft in ratcheting engagement with one another.

BACKGROUND OF THE INVENTION

In orthopaedic surgery, it is not unusual for the surgeon to use a plurality of bone screws to secure a prosthesis to the patient's bone. For example, in a total knee replacement procedure many tibial plateaus rely on bone screws passing through the tibial plateau and into the tibia for initial fixation of the tibial plateau to the bone. Further, in some total hip replacement procedures the acetabular cup is secured within the acetabulum by a plurality of bone screws.

SUMMARY OF THE INVENTION

The bone screw of this invention includes a two piece screw having a ratcheting connection therebetween. The upper portion of the screw shaft includes a plurality of teeth, the head includes a central throughbore for accommodating the toothed screw shaft and includes teeth for engaging the teeth on the screw shaft. The upper end of the screw shaft is fluted. The fluted shaft is engaged by corresponding protuberances in the central bore of the screw head so that the bone screw may be turned into the bone in a normal fashion. Once the screw is seated, downward pressure exerted against the head (as experienced during use) will cause the head to ratchet within the toothed shaft. The teeth on the shaft and the teeth within the central bore of the head are arranged such that the screw head will only shift toward the screw shaft to thereby shorten its length and not allow it to lengthen again. Shifting of the head in the opposite direction would be considered undesirable and is therefore not permitted.

In an alternative embodiment, the screw shaft is not fluted and the upper end of the screw shaft includes an opening to accommodate a turning device such as an Allen wrench or screw driver. The head in the alternative embodiment would include an axial throughbore with ratchet teeth formed therein to accommodate the upper end of the screw shaft. The alternative embodiment permits downward force to be exerted against the screw during insertion without pressing against the head thereby preventing unwanted ratcheting of the head relative to the screw.

Accordingly, it is an object of the invention to provide a novel bone screw.

Another object of the invention is to provide for a novel bone screw having a separate head and shaft.

Another object of the invention is to provide for a novel bone screw having a two piece head and shaft with a ratcheting connection therebetween.

Other objects of the invention will become apparent upon a reading of the following description taken with the accompanying figures.

BRIEF DESCRIPTION OF THE FIGURES

FIG. 3 is an exploded perspective view of an alternative embodiment of the ratcheting bone screw.

DESCRIPTION OF THE PREFERRED EMBODIMENT

The preferred embodiment herein disclosed is not intended to be exhaustive or to limit the invention to the precise form disclosed. Rather, it is chosen and described in order to best explain the invention so that others skilled in the art may utilize its teachings.

Figure 2:
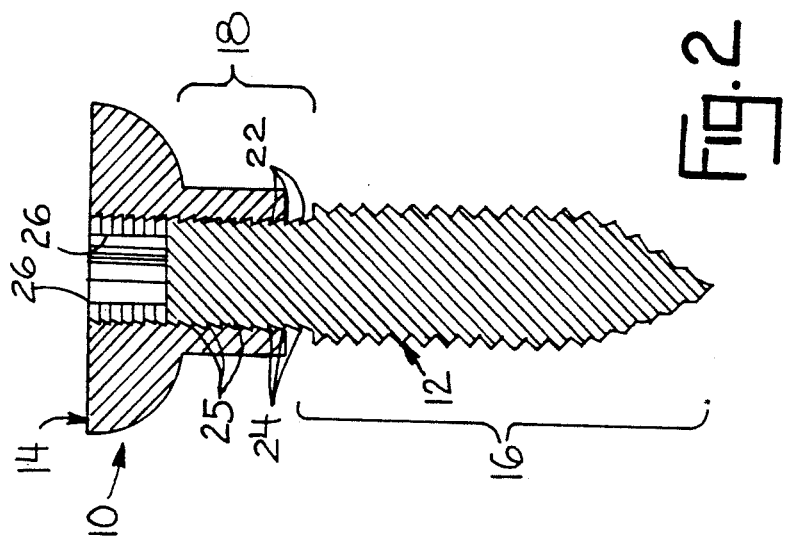
FIG. 2 is a longitudinal sectional view of the bone screw of the invention.
Figure 1:
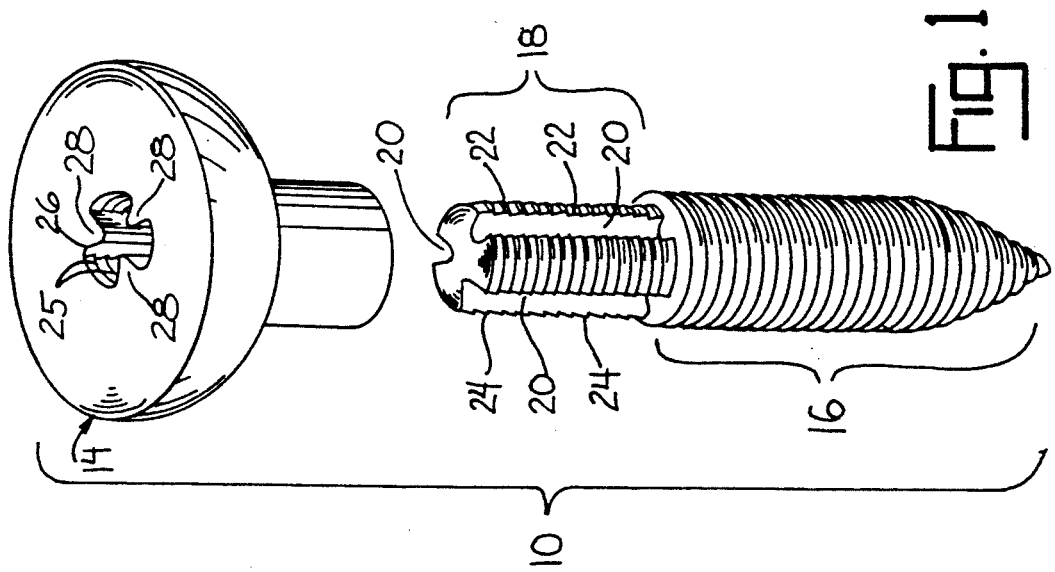
FIG. 1 is an exploded perspective view of the bone screw of the invention.

Referring now to FIGS. 1 and 2, bone screw 10 is illustrated as including a shaft 12 and a separate head 14. Shaft 12 includes a distal portion 16, a proximal portion 18 and defines a longitudinal axis. The distal portion 16 of shaft 12 includes a helical thread. The proximal portion 18 includes a plurality of longitudinal grooves or flutes 20 and a plurality of circumferential grooves 22. Grooves 22 form circumferential teeth 24. Head 14 includes a central longitudinal opening 26. A plurality of protrusions 28 extend into opening 26 and are formed to be slidably accommodated within flutes 20 of shaft 12. A plurality of circumferential teeth 25 are formed within opening 26 of head 14.

In use, head 14 is slid onto the proximal portion 18 of shaft 12 such that protrusions 28 are frictionally accommodated within flutes 20 of shaft 12. Initially, head 14 is spaced from the distal portion of shaft 12 as illustrated in FIG. 2. The surgeon then inserts a driver into the open end of the screw head. The driver (not shown) is preferably formed for a cooperating fit within the center bore of the head. The surgeon rotates the driver, head and shaft to turn the screw into the bone. The fit between the flutes of the stem and the protrusions of the head permit rotation of the screw in a clockwise or counter clockwise direction. After the screw is seated and the patient is using the prosthesis, pressure exerted in a downward direction on the head causes the teeth formed within the central opening of the head to ratchet over the teeth of the proximal portion of the shaft. Thus, the screw under pressure will seek its shortest length and maintain a tight clamping engagement with the article it is connecting to the bone.

Referring now to FIG. 3, an alternative embodiment of the invention is illustrated. Two piece bone screw 30 includes a shaft 32 and a head 34. Shaft 32 includes a continuous helical thread 36 extending over the distal portion 38 of the shaft. The proximal portion 40 of shaft 32 includes a plurality teeth 42 extending circumferentially around the shaft as illustrated in FIG. 3. An opening 44 is formed in the upper end of shaft 32 to accommodate a driving device such as a screw driver or an Allen wrench. It should be understood that the teeth 42 of shaft 32 are oriented in a downwardly angled manner similar to the orientation of teeth 24 of shaft 12. Head 34 includes a central throughbore 46 shaped t accommodate proximal potion 40 of shaft 32. A plurality of teeth 48 are formed within throughbore 46 of head 34. The head is pushed onto the proximal portion of the shaft during production. In use, the surgeon inserts a driver (not shown) into opening 44 of shaft 32 and turns the screw into the bone for clamping engagement as described above. As with the embodiment of FIGS. 1 and 2, once seated downward, pressure on the screw as experienced in use will cause the head to ratchet over teeth 42 of shaft 32 such that the effective length of the screw will shorten to tighten the screw. Since the driver is directly connected to the shaft during insertion, pressure exerted on the screw during insertion is directed through the shaft to prevent unwanted ratcheting of the head relative to the screw during insertion. Throughout the use of the screw, the head and shaft are rotatable relative to one another due to the engagement of the circumferential teeth without shifting the head longitudinally along the shaft.

It should be understood that the proximal portion of the shaft could be formed with a blind bore having a plurality of teeth and the head could be formed having a lower depending toothed shaft for engagement within the blind bore. Such a construction would be considered consistent with the teachings of the invention.

Further, it should be understood that while the central bore of the head is illustrated as passing completely through the head, the bore could be partially through the head with a standard screw driver aperture formed in the head's upper surface. Again, such would be considered within the scope of the invention's teachings.

It should also be understood that any ratcheting mechanism could be used to allow the head to shift relative to the shaft in only one direction.

Finally, it should be understood that the invention is not limited to the precise form disclosed but may be modified within the scope of the appended claims.

I claim:

1. A bone screw having a shaft and a separate head carried by said shaft and longitudinally shiftable relative thereto, said shaft having a proximal portion and a distal portion, said proximal portion having a plurality of circumferential teeth, said distal portion including a helical thread, said head including a plurality of circumferential teeth for ratcheting engagement with said teeth of aid shaft as said head is slid longitudinally relative to said shaft in one direction, said head includes a central throughbore for accommodating the proximal portion of said screw shaft, said teeth of said head extending inwardly into said central bore, said ratcheting engagement of head teeth and the shaft teeth preventing said head from shifting relative to said shaft in a direction other than said one direction, said proximal portion of the shaft including at least one longitudinal groove interrupting the circumferential teeth and extending a substantial portion of said proximal portion, said head including a protuberance extending into said central throughbore for accommodation within said groove to prevent rotation of said head relative to said shaft.

* * * * *